US009757347B2

(12) United States Patent
Nishizawa et al.

(10) Patent No.: US 9,757,347 B2
(45) Date of Patent: Sep. 12, 2017

(54) INGESTION METHOD OF CREATINE COMPOSITION, CREATINE COMPOSITION FOR USING IN THE INGESTION METHOD, AND CREATINE-CONTAINING MEDICAMENT AND FOOD EACH PRODUCED USING THE CREATINE COMPOSITION

(71) Applicant: Hirohisa Nishizawa, Tokyo (JP)

(72) Inventors: Hirohisa Nishizawa, Tokyo (JP); Haruhiko Sueoka, Tokyo (JP)

(73) Assignee: Hirohisa Nishizawa, Tokyo (JP)

( * ) Notice: Subject to any disclaimer, the term of this patent is extended or adjusted under 35 U.S.C. 154(b) by 0 days.

(21) Appl. No.: 14/357,032

(22) PCT Filed: Nov. 9, 2012

(86) PCT No.: PCT/JP2012/079105
§ 371 (c)(1),
(2) Date: May 8, 2014

(87) PCT Pub. No.: WO2013/069764
PCT Pub. Date: May 16, 2013

(65) Prior Publication Data
US 2014/0328910 A1 Nov. 6, 2014

(30) Foreign Application Priority Data
Nov. 10, 2011 (JP) ................ 2011-246208

(51) Int. Cl.
| | |
|---|---|
| *A61K 31/195* | (2006.01) |
| *A61K 9/00* | (2006.01) |
| *A23L 1/305* | (2006.01) |
| *A23L 2/02* | (2006.01) |
| *A23L 2/52* | (2006.01) |
| *A61K 9/08* | (2006.01) |
| *A61K 31/198* | (2006.01) |
| *A23L 33/10* | (2016.01) |
| *A23L 33/175* | (2016.01) |

(52) U.S. Cl.
CPC ............ *A61K 31/195* (2013.01); *A23L 2/02* (2013.01); *A23L 2/52* (2013.01); *A23L 33/10* (2016.08); *A23L 33/175* (2016.08); *A61K 9/0053* (2013.01); *A61K 9/0095* (2013.01); *A61K 9/08* (2013.01); *A61K 31/198* (2013.01); *A23V 2002/00* (2013.01)

(58) Field of Classification Search
USPC ................................. 514/565, 557
See application file for complete search history.

(56) References Cited

U.S. PATENT DOCUMENTS

| | | | |
|---|---|---|---|
| 5,612,375 A | 3/1997 | Sueoka | |
| 5,719,319 A | 2/1998 | Weiss et al. | |
| 5,886,040 A * | 3/1999 | Fang | 514/557 |
| 5,973,005 A * | 10/1999 | D'Amelio et al. | 514/565 |
| 6,093,746 A | 7/2000 | Uchida et al. | |
| 6,399,819 B1 | 6/2002 | Kessel et al. | |
| 2007/0292403 A1* | 12/2007 | Nivaggioli | 424/94.1 |
| 2009/0163739 A1* | 6/2009 | Thalhammer et al. | 562/560 |

FOREIGN PATENT DOCUMENTS

| | | | | |
|---|---|---|---|---|
| CN | 1287118 | * | 3/2001 | ......... C07C 279/14 |
| EP | 0 669 083 | | 8/1995 | |
| EP | 0 911 026 | | 4/1999 | |
| JP | 7-236460 | | 9/1995 | |
| JP | 08-224073 | * | 9/1996 | ............. A23L 2/52 |
| JP | 09-031043 | | 2/1997 | |
| JP | 9-31043 | | 2/1997 | |
| JP | 2001-131065 | | 5/2001 | |
| JP | 2001-181254 | | 7/2001 | |
| JP | 3595373 | | 9/2004 | |
| JP | 2009-532406 | | 9/2009 | |
| JP | 2010-530848 | | 9/2010 | |
| WO | 02/069740 | | 9/2002 | |
| WO | 2007/115799 | | 10/2007 | |
| WO | 2008/151249 | | 12/2008 | |

OTHER PUBLICATIONS

Creatinejournal.com, "Mixing Creatine." www.creatinejournal.com/creatine-supplement-mixing-creatine/; Aug. 9, 2006.*
International Search Report issued Dec. 4, 2012 in International (PCT) Application No. PCT/JP2012/079105.
Supplementary European Search Report dated Jul. 1, 2015, issued in corresponding European Patent Application No. 12 84 7729.

* cited by examiner

*Primary Examiner* — Walter Webb
(74) *Attorney, Agent, or Firm* — Wenderoth, Lind & Ponack, L.L.P.

(57) ABSTRACT

An ingestion method of creatine composition, taking orally the creatine composition with beverage, characterized in that, the creatine composition is taken orally by preparing creatine composition aqueous solution with dissolving the creatine composition over one minute into water heating at 80-100° C. and by mixing the creatine composition aqueous solution with the beverage having ordinary or cool temperature.

6 Claims, 2 Drawing Sheets

[Fig.1]
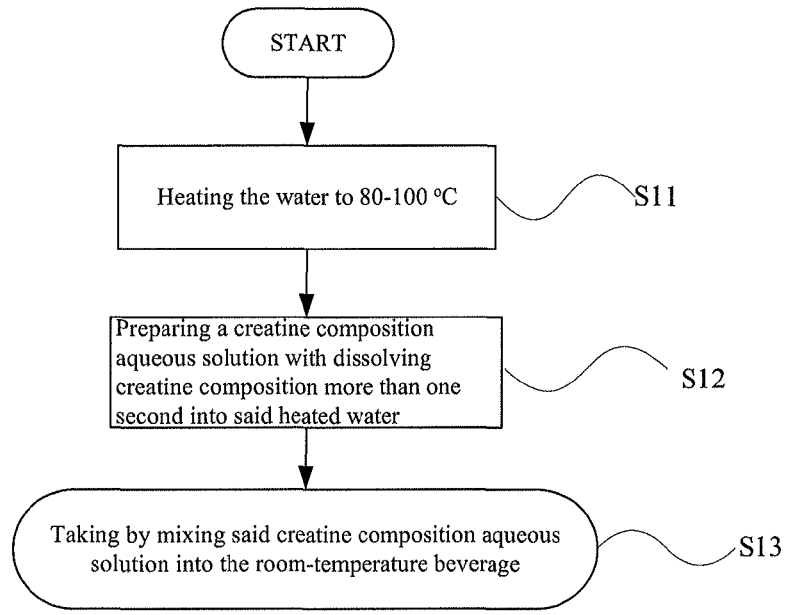
[Fig.2]
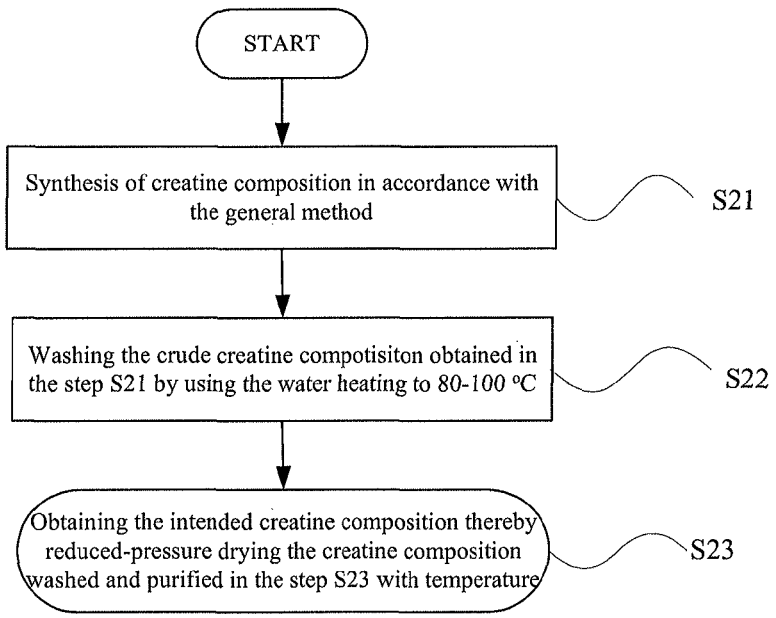

[Fig.3]
(a) The aqueous solution of room temerature
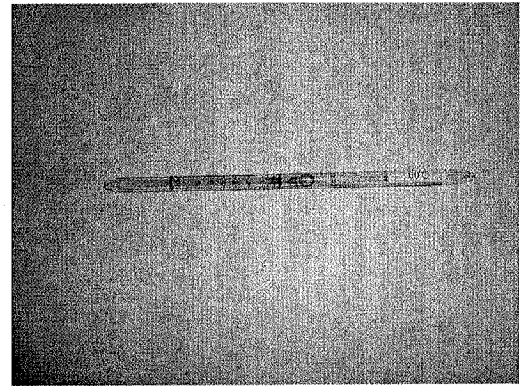
(b) The aqueous solution of 60 °C
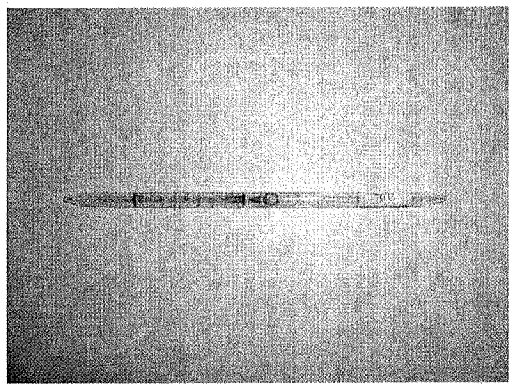
(c) The aqueous solution of 70 °C
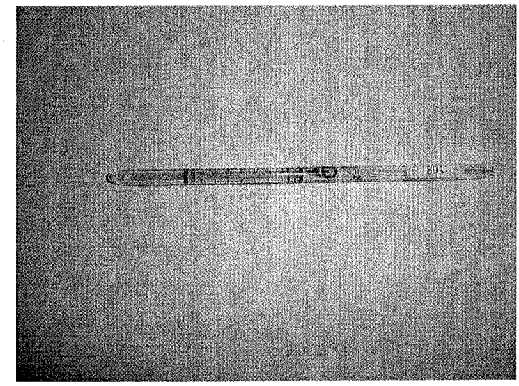
(d) The aqueous solution of 80 °C
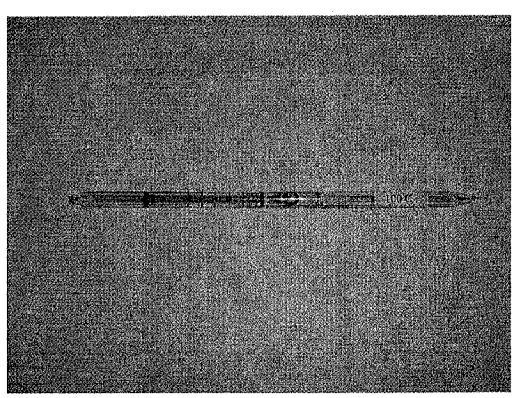
(e) The aqueous solution of 100 °C

INGESTION METHOD OF CREATINE COMPOSITION, CREATINE COMPOSITION FOR USING IN THE INGESTION METHOD, AND CREATINE-CONTAINING MEDICAMENT AND FOOD EACH PRODUCED USING THE CREATINE COMPOSITION

TECHNICAL FIELD

The present invention relates to an ingestion method of creatine composition and a creatine composition for using in the ingestion method, and further relates to a creatine-containing medicament and food each produced using the creatine composition.

BACKGROUND ART

Creatine ((1-methylguanidino) acetic acid) or creatine analog (hereinafter, called "creatine composition") are not designated as a banned substance in IOC (International Olympic Committee) and were known as effectively amino acid composition for an improvement of exercise performance, because the athlete who took the creatine composition officially used by mainly oral ingestion accomplished good results in Barcelona Olympic in 1992. Moreover, a clinical trial for a rare medicinal product for the purpose of a treatment of an interactive disease such as ALS (Amyotrophic Lateral Sclerosis) is also conducted.

Furthermore, the respiratory medicine group of Tsukuba University made a presentation of a affectivity of asthma suppression test by creatine composition by using a guinea pig for laboratory use in 1998 (refer to Non-Patent document 1). In the airway hypersensitivity conference of Japan in next 1999, the same group made certain of the affectivity of asthma suppression for the human by using creatine for seven asthma patients more than two steps aside from the experiment using the asthma-diseased guinea pig (refer to Non-Patent document 2). Moreover, in "A. Nomura et al., Br. J. Pharmacol., 2003, 139, 715-720pp (Non-Patent document 3)", it was certained that creatine had effective against the asthma by finding the anti-inflammatory effect of creatine. In the suppression tests described in Non-patent documents 1 to 3, the creatine-containing beverage developed by the matter applicants etc. was used (for example, Japanese patent publication No. 3595373 (B). Hereinafter, the publication is called "Patent Document 1".). Moreover, the creatine-containing suppression agent is described in American Patent No. 60,937,746 B (called "Patent Document 2").

Here, product types of creatine composition are powder-typed, tablet, capsule, suspension, and aqueous solution, wherein the creatine powder is most used in the selling market of creatine composition, and wherein the ingestion methods, whether directly taking the powder or dissolving the composition in water or juice, are conducted. In case that such methods are general, the report, that the asthma of the mouse for laboratory use takes a turn for the worse by creatine-ingestion, was made in public by the group of Sao Paulo University (refer to Non-patent document 4).

By using the same material as creatine, suppressing the asthma described in Non-patent Documents 1-3 and Patent document 2 while taking a turn for the worse described in Non-Patent document 4 are officially made in public as the research papers.

Basically, creatine is the material contained in meat and fish, and it is possible to take the creatine per gram in the case of freely eating meat and fish. However, so there are no reports that the asthma takes a turn for the worse due to take creatine in food life, creatine itself is not thought to be the cause of asthma inducing or ingravescence.

The commercial creatine is mainly chemical synthetic product and contains a tiny amount of impurities such as creatinine, sodium salt, cyanogen compounds (dihydrotriazine, dicyandiamide), and so on. As well, it is gathered that these impurities cause the asthma inducing or ingravescence. Then, although it is further apprehended that hydrogen cyanide gas is generated by reacting acid substance, such as gastric acid in vivo etc., with the above cyanogen compounds, the sell implementer of creatine has no indications and suggestions about the points in attention when taking creatine.

By the way, in case of producing the creatine-containing beverage described in Patent Document 1, a high-temperature sterilization is deployed on more than 100° C. in final process. On the other hand, generally, the creatine powder is taken by directly intraoral ingestion with ordinary (about 10-35° C.) or cool (less than 10° C.) temperature water or juice, or is taken by dissolving the creatine in ordinary (about 10-35° C.) or cool (less than 10° C.) temperature water or juice as described above. As described above, in case of counting that the asthma suppuration effect described in Non-Patent Documents 1-3 are present in case of using the creatine-containing beverage described in Patent document 1 and that creatine is drunk with ordinary temperature water etc. in the report described in Non-patent Document 4 in reverse, it is inferred that generating with or without hydrogen cyanide gas is related by the temperature of water or juice when taking with creatine or dissolving.

THE LIST OF PRIOR ART DOCUMENT

Patent Document

Patent Document 1: Japanese Patent Publication No. 3595373 B

Patent Document 2: American Patent No. 60,937,746 B

Non-Patent Document

Non-Patent Document 1: Y. Uchida et al., *American Journal of Respiratory and Critical Care Medicine*, Vol. 157, No. 3, A827pp (1998).

Non-Patent Document 2: A. Nomura et al., "study on the effectivity of creatine in the guinea pig of asthma model", The Proceeding of 35th the airway hypersensitivity conference of Japan, Mar. 6th (1999).

Non-Patent Document 3: A. Nomura et al., *Br. J. Pharmacol.*, 2003, 139, 715-720pp.

Non-Patent Document 4: Rodlfo P. Vieira et al., *American Journal of Respiratory Cell and Molecular Biology*, Vol. 37, 660-667pp (2007).

SUMMARY OF THE INVENTION

Problems to be Solved by the Invention

It is an object of the present invention to provide an ingestion method of creatine composition and a creatine composition for using in said ingestion method.

It is also an object of the present invention to provide a creatine-containing medicament and food each using said creatine composition.

Means for Solving the Problems

In order to accomplish the present invention, an ingestion method of creatine composition, taking orally the creatine composition with beverage, characterized in that, said creatine composition is taken orally by preparing creatine composition aqueous solution with dissolving said creatine composition over one minute into water heating at 80-100° C. and by mixing said creatine composition aqueous solution with said beverage having ordinary or cool temperature.

Moreover, in order to accomplish the present invention, said creatine composition is any one of crystalline powder selected from creatine monohydrate, creatine anhydrate, creatine phosphoric salt, creatine pyruvate, or creatine citrate, or wherein said creatine composition is made of two upward of crystalline powders selected from creatine monohydrate, creatine anhydrate, creatine phosphoric salt, creatine pyruvate, or creatine citrate, or wherein said beverage is water, or wherein said water is selected from tap water, distilled water, or group of mineral water, or wherein said beverage is group of juice.

In order to accomplish the present invention, a creatine composition, for use in the ingestion method according to the invention, is characterized in that, an impure substance is removed by washing a crude product obtained in the process of preparing said creatine by water heating at 80-100° C. over one minute.

Moreover, in order to accomplish the present invention, said creatine composition is any one of crystalline powder selected from creatine monohydrate, creatine anhydrate, creatine phosphoric salt, creatine pyruvate, or creatine citrate, or wherein number of times of said washing is/are at least over once.

Moreover, in order to accomplish the present invention, a creatine-containing medicament, using the creatine composition according to the invention, is characterized in that, said creatine-containing medicament is any type selected from powder, granule, tablet, or material coated by capsule or enteric coated drug.

Moreover, in order to accomplish the present invention, a creatine-containing food, using the creatine composition according to the invention, is characterized in that, said creatine-containing food is any type selected from powder, granule, tablet, or material coated by capsule or enteric coated drug.

Advantageous Effects of the Invention

According to the ingestion method of the present invention, it is possible to safely and easily take the creatine composition without impairing the effective ingredient of creatine and considering the concern of the generating of hydrogen cyanide gas.

Moreover, according to the creatine composition of the present invention, there is no concern of the cyanogen compound impurities.

BRIEF DESCRIPTION OF THE DRAWINGS

In the accompanying drawings:
FIG. 1 is a flowchart showing an embodiment of the ingestion method of creatine composition in the present invention;
FIG. 2 is a flowchart showing the creatine composition for using in the ingestion method in the present invention; and
FIG. 3 is the images showing hydrogen cyanide gas detecting tubes in the present examples.

MODE FOR CARRYING OUT THE INVENTION

Hereinafter, the ingestion method of creatine composition in the present invention (hereinafter called "the present ingestion method") will now be explained in more detail.

First, although the beverage using for the present ingestion method can be selected from water, juice, commercial sports drink, milk or dairy products, class of tea, class of coffee, carbonated drink, refreshing drink or anyone, water is preferable therein. Moreover, water is selected from distilled water, tap water, bottled (mineral) water or anyone. The class of mineral water in which is defined the present invention means according to "The descriptive labeling guideline of class of mineral water" (Ministry of Agriculture, Forestry and Fisheries (Japan)) or according to the rules like said guideline in other countries. By the way, water hardness is no qualified. In case of using water may directly use, may arbitrarily add alkali normal solution etc., and may run water through alkali ion exchange means etc.

Next, the creatine composition for using in the ingestion method in the present invention will now be explained in more detail. First, the creatine composition of the present invention means a creatine crystalline powder. Furthermore, the creatine crystalline powder of the present invention is selected from the group of creatine compounds, such as creatine anhydride, creatine monohydrate, mixture of creatine anhydride and monohydrate, creatine phosphate, creatine pyruvate, creatine citrate, creatine maleic acid ester, creatine malate, creatine methyl ester, creatine ethyl ester, creatine phosphoric acid ester, creatine organonitrate, creatine sulfuric acid ester, creatine leucinate, creatine gluconate, or cyclocreatine, or is furthermore the crystalline powder of creatine analog compounds etc.

Then, the present ingestion method will now be explained in more detail based on a flowchart in FIG. 1. Here is prepared for the case of using the crystalline powder of creatine monohydrate as creatine composition.

Firstly, water is warmed at 80-100° C. (1 atm) (Step S11). Here, in case of adding alkali normal solution etc. to water is to add before heating. About the alkali normal solution herein, the pH (hydrogen ion concentration) of water or beverage for dissolving the creatine composition makes at the range of 7-10. The variety of the alkali normal solution is not only especially limited as long as aqueous solution of weakly basic materials (e.g. Sodium carbonate aqueous solution etc.) which infects human body small, when ingestion, but the concentration of the alkali normal solution is also no limited. As well, the alkali normal solution does not have to be added.

Although the temperature for heating may have the creatine composition dissolve over the boiling point of water (about 100° C.) with applying pressure on water which is into pressure vessel for the purpose of turning up the solubility, the upper limit of the temperature sets 100° C. (the boiling point of water) because the creatine composition is taken orally and the creatine composition itself has the possibility of causing denaturation (mainly, the decomposition etc. of creatine itself that is main component.). Moreover, in case that the heating temperature is less than 80° C., the composition cannot only well dissolve, with taking the composition, there is the possibility of the degradation of asthma as shown in BACKGROUND ART because a tiny amount of impurities (mainly cyanide compounds) contained in creatine composition, which cannot degrade and remove, react with the acid substance such as gastric acid in human body etc. As will hereinafter be described in detail of these things by using the examples.

After the Step S11, the creatine composition aqueous solution is prepared by dissolving the creatine composition over one second (Step S12).

With regard to the dissolution time, if less than one second, the creatine composition does not dissolve enough, and a tiny amount of impurities contained in the creatine composition are not degraded and removed. Moreover, although the upper limit of the dissolution time is not limited, the time is until about ten minutes (600 seconds) in case of taking account of the denaturation of the creatine composition itself etc. As well, so the whole aqueous solution may be homogeneous when dissolving the creatine composition into water, the amount of water and creatine are not limited.

Next, after the Step S12, the creatine composition is taken by mixing said creatine composition aqueous solution into the beverage at normal (about 10-35° C.) or cool (less than 10° C.) temperature (Step S13). As presented above, although such beverage is non-limiting, but is not limited to water, juice, and commercial isotonic drink etc., water is preferably in these. As well, the water using as beverage makes no difference whether using the same water or the different water which is used with preparing said creatine composition aqueous solution.

As well, with regard to the beverage and the creatine composition in the present ingestion method, we explain in case of using the creatine crystalline powder (mainly creatine monohydrate) as the creatine composition, but no limited, it is possible that we use the various beverage for dissolving creatine and use the crystalline powder of the above creatine compounds or creatine analogs instead of creatine monohydrate as the creatine composition. Moreover, the creatine composition are taken with food, food additive, or medicine for controlling the acid substance such as gastric acid etc. at the same time.

Next, we explain about the creatine composition for mainly using in the present ingestion method. As well, the embodiment is explained by assuming the crystalline powder of creatine monohydrate (merely hereinafter called "the creatine crystalline powder") as the creatine composition.

Generally, as presented above, a tiny amount of impurities, such as sodium salt, cyanide etc., are contained in the (general commercial) creatine crystalline powder. For example, removing the impurities by recrystallization treatment is thinkable, however, in case of oral ingestion has to be careful because in case of using recrystallization treatment has to examine the select of solvent for use, and the perfect removing the solvent component is difficult depending on the solvent for use.

Moreover, although it is possible to remove the impurities (mainly cyanide) in case commercial product by using the present ingestion method, the present ingestion method has not shown that it is possible to perfectly remove depending on the amount of the impurities.

Here, with regard to the creatine composition (assuming the crystalline powder of creatine monohydrate), in the previous step to use in the present ingestion method, i.e., in the step of product, we have studied the creatine composition much removing the impurities. Hereinafter, we explain for the basis of flowchart shown in FIG. 2.

With regard to the creatine composition (herein, meaning of the crystalline powder of creatine monohydrate), the synthetic reaction of creatine composition is done in accordance with general (synthetic) method (Step S21). As well, the general method herein can be found in, for example, Japanese Patent Publication No. 2009-532406A (or corresponding to WO2007/115799). Incidentally, in the method described in Japanese Patent Publication No. 2009-532406A, after sodium sarcosinate solution is obtained by reacting between N-methanol amine and sodium hydroxide aqueous solution in autoclave unit in the presence of raney-Ni catalyst based on copper/nickel, creatine monohydrate is obtained by preparing pH 9.6 and reacting between said sodium sarcosinate solution and cyanamide (see examples 1 and 3 in Japanese Patent Publication No. 2009-532406A). In case preparing the creatine composition by the synthetic reaction in said publication or the general method, the Step S21 is stopped at the step of obtaining the reaction crude compound.

The crude compound obtained in the Step S21 is washed over one second by water heating to 80-100° C. (Step S22). In this case, water is preferably pure water, but tap water. As well, the degradation and removing of the impurities are not enough if the heating temperature of water is less than 80° C., and creatine itself which is mainly component of the creatine composition has the possibility of degradation if the heating temperature of water is more than 100° C. Moreover, the time(s) of washing is/are not limited if over 1 time, however, the times are preferably until about 10 times.

Next, the intended creatine composition is obtained by reduced-pressure drying the creatine composition washed and purified in the Step S22 used by vacuum oven etc. (Step S23). The pressure when reduced-pressure drying is not especially limited. Moreover, the pressure when reduced-pressure drying is preferably about 40-100° C. That is, the pressure is arbitrarily adaptable because of reduced-pressure drying for removing water.

As well, in regard to said creatine composition, the embodiment is explained about the crystalline powder of creatine monohydrate as an example, however, the embodiment can be applied to the crystalline powder of the other creatine composition, such as creatine anhydrate, mixture of creatine anhydrate and monohydrate, creatine phosphate, creatine pyruvate, creatine citrate, creatine maleic acid ester, creatine maleate, creatine methyl ester, creatine ethyl ester, creatine phosphoric acid ester, creatine nitric acid ester, creatine sulfuric acid ester, creatine leucinate, creatine gluconate, and cyclocreatine etc., or further the crystalline powder of the other creatine analogs etc.

Moreover, it is possible to apply the food selected from powder type, tablet form, granular type, suspension type or coated by capsule or enteric coated drug and the creatine-containing medicine selected from powder type, tablet form, granular type, suspension type or coated by capsule or enteric coated drug. As well, with regard to said capsule and enteric coated drug, the material quality of them are no especially limited because reacting between gastric acid and the component of creatine can have to be controlled.

As presented above, the ingestion method of creatine composition and the creatine composition for using in said ingestion method in the present invention are explained, the embodiments of the present invention are no limited.

EXAMPLES

The examples of the ingestion method of creatine composition in the present invention are explained as follows.

Example 1

With or without a Generation of Hydrogen Cyanide Gas by Reacting Between the Creatine Aqueous Solution and Hydrochloric Acid Under Various Temperatures As presented above, the generation of hydrogen cyanide gas by reacting between the creatine composition taken in human body and gastric acid in human body is thought, in addition, some relationships with the water temperature for dissolving the creatine composition are thought.

And so, to review the above presumption, we made an experiment for reacting between creatine and hydrochloric acid by dissolving the creatine composition in to the water having various temperatures.

First, 2 grams of creatine monohydrate (hereinafter, "creatine" in Example 1) as the creatine composition were added to pure water (hereinafter, merely called "water") having normal temperature 5 mL and stirred in beaker. The normal temperature herein means the thing at the range of about 10-35° C. After said stirring, the aqueous solution was changed into a conical flask, was added hydrochloric acid 10 mL, was dissolved by stirring the conical flask with stopple, and was determined by using hydrogen cyanide gas detecting tube (GV-100S manufactured by GASTEC Corporation. The determining range of 0.2-0.7 ppm) three minutes after said dissolving. At this time, the detecting tube gave pink color, and 0.2 ppm of hydrogen cyanide gas was detected (see FIG. 3 (a)).

Also, the pure water was each prepared at 60, 70, 80 and 100° C., wherein we made the experiments by the similar process to the above process as needed. As a result, in case that the temperature of the water was each 60 and 70° C., the detecting tube gave pink color in common with using the pure water having normal temperature, and 0.2 ppm of hydrogen cyanide gas was detected (see FIGS. 3(b) and (c)). Moreover, in case that the temperature of the water was 80° C., hydrogen cyanide gas was less than 0.2 ppm, that is, the detecting tube didn't give pink color shown in FIG. 3 (a)-(c), and in case that the temperature of the water was 100° C., the detecting tube didn't give a color, and it followed that hydrogen cyanide gas was not detected. As well, the relationship between the temperature of pure water and the concentration of hydrogen cyanide gas is shown in follow Table 1.

TABLE 1

The relationship between the temperature of water and the concentration of hydrogen cyanide gas

| | Temperature of water (° C.) | | | | |
|---|---|---|---|---|---|
| | Normal temperature | 60 | 70 | 80 | 100 |
| Concentration of HCN (ppm) | 0.2 | 0.2 | 0.2 | <0.2 | No detected |

As the above result, in the case of using the normal temperature water to creatine, as well as, the case of using 60 and 70° C. water to creatine, the risk that hydrogen cyanide gas was generated was recognized. On the other hand, it was recognized that hydrogen cyanide gas was less than 0.2 ppm in 80° C. water and was no generated in 100° C. water. From this thing, in case of grading and removing the cyanide compounds, which were infinitesimally contained in creatine monohydrate, in the warm water more than 80° C., the risk that hydrogen cyanide gas was generated was indicated.

Next, in the ingestion method for creatine composition in the present invention, the animal test using guinea pig was run to recognize the effect in case using creatine (creatine monohydrate) by dissolving into normal temperature (about 10-35° C.) water in the ingestion method. Hereinafter, the animal tests as Examples 2-8 were explained.

Example 2

Preparations of a Creatine Test Article Solution and a Control Experiment Solution (1) Preparation of the Creatine Test Article Solution First, in Example 2, we prepared the creatine test article solution and the control experiment solution. The creatine composition and the medium used when preparing the creatine test article solution are given follow Table 2.

TABLE 2

The reagants using for the preparation of the creatine test article solution in Example 2.

| Reagent | Proffer (manufacture) source | Strage condition |
|---|---|---|
| Creapure ™ [as creatine monohydrate] | Immuno Bio Japan incorporated | Cold place (1~15° C.) |
| 0.5 w/v % methyl cellurose 400solution [as medium] | Wako Pure Chemical Industries, Ltd. | Cold place (1~15° C.) |

After weighing a necessary quantitative creatine monohydrate (hereinafter called "creatine powder"), the creatine test article solution was prepared by grinding the creatine powder by agate mortar and suspending the powder by adding appropriate quantities of medium. The necessary quantitative herein means as administering 3000 mg creatine powder to guinea pig 1 kg.

Next, the obtained creatine powder suspension solution was prepared by pouring to measuring cylinder or flask in such a way that the concentration of the suspension solution was 300 mg/mL by further adding the medium. As well, the preparation of the creatine test article solution was prepared at time of use, that is, prepared as needed per oral administration described below (Examples 5 and 6).

(2) Preparation of the Control Experiment Solution 0.5 w/v % methyl cellulose 400 solution (normal temperature), shown in Table 2, as control experiment solution was used.

Example 3

Preparations of Reagents for Use in Examples 5 and 6

There are explained next about preparations of antigen-containing normal saline solution (1 w/v % and 2 w/v %), metyrapone normal saline solution and pyrilamine maleate normal saline solution.

(1) Preparations of Antigen-Containing Normal Saline Solutions (1 w/v % and 2 w/v %)

First, Ovalbumin (Sigma-Aldrich. Hereinafter, "OVA") was used as the antigen. The preparations were made so as to 1 w/v % and 2 w/v % OVA-containing normal saline solutions by using normal saline solution (Otsuka Pharmaceutical Co. Ltd.) after weighing OVA. The respective preparations was prepared at time of use, that is, prepared as needed with respect to oral administration experiment hereinafter (see Examples 5 and 6).

(2) Preparation of Metyrapone Normal Saline Solution

Metyrapone for using was used of Sigma-Aldrich. The preparation was made so as to 10 mg/mL metyrapone-containing normal saline solution by using normal saline solution (Otsuka Pharmaceutical Co. Ltd.) after weighing metyrapone. As well, the preparation was also prepared at time of use as with said OVA-containing normal saline solution.

(3) Preparation of Pyrilamine Maleate Normal Saline Solution

Pyrilamine maleate for using was used of Sigma-Aldrich. The preparation was made so as to 10 mg/mL pyrilamine maleate-containing normal saline solution by using normal saline solution (Otsuka Pharmaceutical Co. Ltd.) after weighing pyrilamine maleate. As well, the preparation was also prepared at time of use as with said OVA-containing normal saline solution.

Example 4

Administrations of the Creatine Test Article Solution and the Control Experiment Solution Prepared in Example 2

Before tests of examples 5 and 6 hereinafter, the creatine test article solution and the control experiment solution prepared in Example 2 were respectively administered to two guinea pigs (supplied by Kyudo Co., Ltd.). Hereinafter, the guinea pig administered the creatine test article solution is called "creatine asthma model guinea pig", and the guinea pig administered the control experiment solution is called "control asthma model guinea pig".

The guinea pigs for using (in Example 4) were male and 5 weeks old both two guinea pigs. As well, the guinea pigs used other guinea pigs in each case depending on the number of the respective experiments of Examples 5 and 6 hereinafter. In the oral administration, the respective body weights of the guinea pigs was measured before administering. Next, the each amount of the creatine test article solution and the control experiment solution was respectively calculated for the basis on the respective body weights which was previously measured as 10 mL per the guinea pig 1 kg.

And, about the oral administration, the guinea pigs were administrated by using syringe and sustenance catheter and were once administrated before one hour of the respective tests on Examples 5 and 6.

Example 5

Preparation of a Creatine Asthma Model Guinea Pig

After respectively sending the guinea pig administering the creatine test article solution (creatine asthma model guinea pig) and the guinea pig administering the control experiment solution (control asthma model guinea pig) both prepared in Example 4 to container made of polypropylene, they were given 1 w/v % OVA-containing normal saline solution prepared in Example 3 at ten minutes per one day and constantly eight days with nebulizing said OVA-containing normal saline solution by using ultra-sonic wave nebulizer. Thus, the creatine asthma model guinea pig was prepared.

Example 6

Initiate Experiment of Asthma Reaction

With respect to the creatine asthma model guinea pig and the control asthma model guinea pig both prepared in Example 5, the respective antigen-antibody reactions of them was initiated by giving the mist of 2 w/v % OVA-containing normal saline solution prepared in Example 3 at 5 minutes used by ultra-sonic wave nebulizer after sending and retaining the guinea pigs a week later of a final sensitization. The respective asthma model guinea pigs was administered the metyrapone normal saline solution prepared in Example 3 into the respective hind-limb peripheral veins at about 24 hours (±five minutes) and 1 hour (±five minutes) before said initiate and the pyrilamine maleate normal saline solution prepared in Example 3 into the respective ventral cavities at 30 minutes before said initiate.

As well, the each amount of the metyrapone normal saline solution and the pyrilamine maleate normal saline solution for administration was calculated in increments of 0.1 mL, on the basis of the weight previously measured before administrating said normal saline solutions, as 10 mg/mL per 1 kg of the respective guinea pigs.

Example 7

Measurement of Airway Resistance

In Example 7, with regard to the creatine asthma model guinea pig and the control model guinea pig, the respective airway resistances (specific airway resistance, sRaw) of them was measured by using total respiratory function analysis system (Pulmos-I, MIPS Co., Ltd.). The measurement of the sRaw value measured at one minute later of the initiate of the antigen-antibody reaction in Example 6 and at 2, 4, 5, 6, 7, 8 and 22 (−24) hours later of said antigen-antibody reaction. The sRaw value in the respective measurement times was the mean value of 100 times respiratory rates of the respective guinea pigs. As well, with regard to the respective guinea pigs, before administering the metyrapone normal saline solution of Example 6, a naturalization for a chamber for respiratory function measurement was given by performing the operation to send and retain in said chamber at least once.

Next, the sRaw increasing rate in regard to the sRaw value depending on the respective measurement times was calibrated by using the analysis soft (WinPUL16Ver. 1.23, MIPS Co., Ltd.) of the total respiratory function analysis system. As well, the sRaw increasing rate is shown as follow formula.

$$\text{sRaw increasing rate of respective measurement time}(\%) = \frac{\text{sRaw value of respective measurement times} - \text{sRaw value before initiation}}{\text{sRaw value before initiation}} \times 100 \quad \text{[Formula 1]}$$

Moreover, the sRaw increasing rate in the respective measurement times is shown in next Table 3. As a result in Table 3, the sRaw increasing rates both the creatine asthma model guinea pig and the control asthma model guinea pig once had reductive peak in four hours later from the initiate of the antigen-antibody reaction, whereas they had increased peak in five and six hours later from the initiate of the antigen-antibody reaction. And, the sRaw increasing rate in seven hours later from the initiate of the antigen-antibody reaction in the creatine asthma model guinea pig was increasing, whereas the sRaw increasing rate in seven hours later from the initiate of the antigen-antibody reaction in the control asthma model guinea pig was decreasing. In regard to eight and 23-24 hours later from the initiate of the antigen-antibody reaction, the sRaw increasing rates both the creatine asthma model guinea pig and the control asthma model guinea pig had decreasing trend. As well, the sRaw increasing rate of the creatine asthma model guinea pig (exclude one minute later from the initiate of the antigen-antibody reaction) was totally higher than that one of the control model guinea pig.

TABLE 3 sRaw increasing rate of the respective measurement times.

| respective measurement times (from starting the initiation of the antigen-antibody reaction) | sRaw increasing rate (%) (creatine asthma model guinea pig) | sRaw increasing rate (%) (control asthma model guinea pig) |
| --- | --- | --- |
| One minute later | 546.48 (±124.24)[*] | 627.40 (±152.22)[*] |
| Two hours later | 51.58 (±5.75)[*] | 82.91 (±30.11)[*] |
| Four hours later | 46.79 (±31.93)[*] | 14.84 (±8.36)[*] |
| Five hours later | 88.88 (±21.26)[*] | 70.44 (±23.26)[*] |
| Six hours later | 113.04 (±47.37)[*] | 95.66 (±18.29)[*] |
| Seven hours later | 153.61 (±42.34)[*] | 70.59 (±18.53)[*] |
| Eight hours later | 68.04 (±12.90)[*] | 36.64 (±8.64)[*] |
| 23-24 hours later | −8.27 (±8.79)[*] | −3.09 (±9.58)[*] |

[*]The values in bracket are error ranges.

Example 8

Appraisals of Immediate Asthmatic Reaction (IAR) and Late Asthmatic Reaction (LAR)

In the sRaw increasing rate calibrated in the above Example 7, the sRaw increasing rate which was the initiation of the antigen-antibody reaction at one minute later was identified as an estimative index of immediate asthmatic reaction (hereinafter, called "IAR").

Moreover, the sRaw increasing rates which were the initiation of the antigen-antibody reactions at 4-8 hours later were identified as an estimative index of late asthmatic reaction (hereinafter, called "LAR"). As well, with regard to the estimative index of LAR, AUC4-8 h that is the area under the curve calibrated on the basis of the sRaw increasing rates which were the initiation of the antigen-antibody reactions at 4-8 hours later was identified as the estimative index. The calibration method of AUC4-8 h is subjected to the formula shown in Formula 2. Moreover, the respective IAR and LAR of the creatine asthma model guinea pig and the control asthma model guinea pig are shown in Table 4.

$$AUC4\text{-}8\ h(\%) = \tfrac{1}{2}(\%sRaw.4\ h + \%sRaw.8\ h) + (\%sRaw.5\ h + \%sRaw.6\ h + \%sRaw.7\ h)$$

%sRaw.*h: sRaw increasing rate at * hours later from starting the initiation [Formula 2]

TABLE 4

The appraisals of immediate asthmatic reaction (IAR) and late asthmatic reaction (LAR) in the respective asthma model guinea pigs.

| Model guinea pig | sRaw increasing rate of IAR (%) | AUC4-8 h of LAR (%) |
| --- | --- | --- |
| "creatine asthma model" | 546.48 (±124.24)[*] | 412.95 (±120.07)[*] |
| "control asthma model" | 627.40 (±152.22)[*] | 262.43 (±45.98)[*] |

[*]The values in bracket are error ranges.

In case of studying IAR and LAR, because the creatine asthma model guinea pig had higher value of LAR than the control asthma model guinea pig, it turned out that the creatine asthma model guinea pig caused stronger asthma symptom. Although the effectivity of the ingestion method for creatine and the relationship between hydrogen cyanide gas and the asthma symptom in the present invention have the various room to study, the relationship between the generation of hydrogen cyanide gas and the temperature of the medium shown in Example 1 and the result of the experiment of the asthma model guinea pigs in Examples 6 to 8 suggest the relationship between the asthma symptom and hydrogen cyanide gas because the strong asthma symptom was caused in case of taking with dissolving the creatine composition into the room-temperature (about 10-35° C.) medium at least.

Although we explain the examples of the present ingestion method for creatine composition, the various conditions with the creatine composition, the temperature for heating, and the animal experiment with guinea pigs are not limited so the present examples are merely said examples.

The invention claimed is:

1. A method for orally taking commercial creatine crystalline powder with a beverage having an ordinary or cool temperature, comprising the steps of:
    heating water at 80-100° C.;
    preparing a creatine crystalline powder aqueous solution by dissolving said commercial creatine crystalline powder in said heated water for 1-600 seconds; and
    taking said commercial creatine crystalline powder aqueous solution by mixing with said beverage having an ordinary or cool temperature.

2. The method according to claim 1, wherein said commercial creatine crystalline powder is any one of the group of creatine compounds selected from creatine monohydrate, creatine anhydrate, creatine phosphoric salt, or creatine citrate.

3. The method according to claim 1, wherein said commercial creatine crystalline powder is two upward of the group of creatine compounds selected from creatine monohydrate, creatine anhydrate, creatine phosphoric salt, or creatine citrate.

4. The method according to claim 1, wherein said beverage is identical with or different from the water used in preparing said creatine crystalline powder aqueous solution.

5. The method according to claim 4, wherein said water is selected from tap water, distilled water, or group of mineral water.

6. The ingestion method according to claim 1, wherein said beverage is group of juice.

* * * * *